United States Patent
Morman et al.

(10) Patent No.: US 7,393,346 B2
(45) Date of Patent: Jul. 1, 2008

(54) DISPOSABLE LEAK-PROOF CONTAINMENT GARMENT

(75) Inventors: Michael Tod Morman, Alpharetta, GA (US); Thomas Harold Roessler, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 473 days.

(21) Appl. No.: 10/325,875

(22) Filed: Dec. 20, 2002

(65) Prior Publication Data

US 2004/0122393 A1 Jun. 24, 2004

(51) Int. Cl.
*A61F 13/15* (2006.01)
*A61F 13/20* (2006.01)

(52) U.S. Cl. .............. 604/385.01; 604/367; 604/369; 604/373

(58) Field of Classification Search ......... 604/358–402; 2/464–466, 400–409, 2.11–2.14, 227–243; 602/60, 67; 128/202.11; 600/19, 20
See application file for complete search history.

(56) References Cited

U.S. PATENT DOCUMENTS

| | | | |
|---|---|---|---|
| 3,072,123 A * | 1/1963 | Davis | 604/366 |
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,613,687 A | 10/1971 | Kennedy | |
| 3,692,618 A | 9/1972 | Dorschner et al. | |
| 3,751,727 A * | 8/1973 | Shepard et al. | 2/2.14 |
| 3,802,817 A | 4/1974 | Matsuki et al. | |
| 3,894,542 A * | 7/1975 | Sacristan | 450/123 |
| 3,909,847 A * | 10/1975 | Holt et al. | 2/465 |
| 3,916,900 A | 11/1975 | Breyer et al. | |
| 4,084,584 A * | 4/1978 | Detty | 602/26 |
| 4,340,563 A | 7/1982 | Appel et al. | |
| 4,639,949 A | 2/1987 | Ales et al. | |
| 4,646,362 A | 3/1987 | Heran et al. | |
| 4,652,487 A | 3/1987 | Morman | |
| 4,655,760 A | 4/1987 | Morman et al. | |
| 4,657,802 A | 4/1987 | Morman | |

(Continued)

FOREIGN PATENT DOCUMENTS

EP  0 274 752  7/1988

(Continued)

OTHER PUBLICATIONS

*Under-Ease*, www.under-tec.com, 1 page.

*Primary Examiner*—Tatyana Zalukaeva
*Assistant Examiner*—Michael G Bogart
(74) *Attorney, Agent, or Firm*—Armstrong Teasdale LLP

(57) ABSTRACT

A disposable, leakproof, containment garment for a wearer is formed from a liquid-impermeable containment shell in a substantially humanoid shape with elastic marginal seal areas, such as torso and appendage margins. The elastic margins are designed to conformably surround the torso and appendages of the wearer and form tensioned and liquid-tight seals against the skin of the wearer when donned. By forming liquid tight seals against the body of the wearer, the garment is favorably constructed to utilize the full capability of any absorbent structures placed within the shell.

23 Claims, 9 Drawing Sheets

U.S. PATENT DOCUMENTS

| | | | |
|---|---|---|---|
| 4,663,220 A | 5/1987 | Wisneski et al. | |
| 4,690,681 A | 9/1987 | Haunschild et al. | |
| 4,699,620 A * | 10/1987 | Bernardin | 604/385.25 |
| 4,701,175 A | 10/1987 | Boland et al. | |
| 4,720,415 A | 1/1988 | Vander Wielen et al. | |
| 4,741,949 A | 5/1988 | Morman et al. | |
| 4,771,483 A * | 9/1988 | Hooreman et al. | 2/237 |
| 4,781,966 A | 11/1988 | Taylor | |
| 4,789,699 A | 12/1988 | Kieffer et al. | |
| 4,880,424 A | 11/1989 | Rautenberg | |
| 4,938,753 A | 7/1990 | Van Gompel et al. | |
| 4,938,757 A | 7/1990 | Van Gompel et al. | |
| 4,959,047 A * | 9/1990 | Tripp, Jr. | 600/19 |
| 4,965,122 A | 10/1990 | Morman | |
| 4,981,747 A | 1/1991 | Morman | |
| 5,114,781 A | 5/1992 | Morman | |
| 5,116,662 A | 5/1992 | Morman | |
| 5,127,896 A * | 7/1992 | de Gaston | 600/20 |
| 5,210,882 A | 5/1993 | Moretz et al. | |
| 5,226,992 A | 7/1993 | Morman | |
| 5,336,545 A | 8/1994 | Morman | |
| 5,352,711 A | 10/1994 | DesMarais | |
| 5,476,458 A * | 12/1995 | Glaug et al. | 604/378 |
| 5,593,398 A | 1/1997 | Weimer | |
| 5,593,400 A | 1/1997 | O'Leary | |
| 5,685,874 A * | 11/1997 | Buell et al. | 604/396 |
| 5,746,731 A | 5/1998 | Hisada | |
| 5,779,658 A * | 7/1998 | Saca | 602/61 |
| 5,883,028 A | 3/1999 | Morman et al. | |
| 5,932,497 A | 8/1999 | Morman et al. | |
| 5,957,878 A * | 9/1999 | Gilliam | 602/60 |
| 6,009,565 A * | 1/2000 | Carrington | 2/455 |
| 6,041,446 A * | 3/2000 | Braunstein et al. | 2/400 |
| 6,083,212 A | 7/2000 | Kumasaka | |
| 6,120,487 A | 9/2000 | Ashton | |
| 6,168,585 B1 | 1/2001 | Cesco-Cancian | |
| 6,224,538 B1 * | 5/2001 | Wang et al. | 600/19 |
| 6,261,278 B1 | 7/2001 | Chen et al. | |
| 6,336,921 B1 | 1/2002 | Kato et al. | |
| 6,414,217 B1 | 7/2002 | Uitenbroek et al. | |
| 6,582,412 B2 * | 6/2003 | Christoffel et al. | 604/385.01 |
| 7,083,604 B2 * | 8/2006 | Sakaguchi | 604/396 |
| 2001/0008027 A1 | 7/2001 | Duplock | |
| 2002/0099346 A1 * | 7/2002 | Strobl | 604/367 |
| 2003/0115660 A1 * | 6/2003 | Hopkins | 2/400 |
| 2004/0092904 A1 * | 5/2004 | Macedo et al. | 604/396 |

FOREIGN PATENT DOCUMENTS

| | | |
|---|---|---|
| EP | 0 217 032 B1 | 2/1992 |
| WO | WO 99/60972 | 12/1999 |
| WO | WO 00/07468 A2 * | 2/2000 |
| WO | WO 02/34184 A1 | 5/2002 |

* cited by examiner

TABLE I part 1

| SECONDS | PRESSURE—INCHES OF WATER | | | |
|---|---|---|---|---|
| | present invention | ULTRATRIM | PAMPERS PREM | PCT 02/34184 A1 |
| 1-15 | 0.00 | -0.01 | 0.01 | 0.00 |
| 16 | 0.00 | 0.25 | 0.07 | 0.11 |
| 17 | 0.21 | 0.26 | 0.31 | 0.62 |
| 18 | 1.43 | 0.26 | 0.31 | 0.62 |
| 19 | 2.35 | 0.26 | 0.31 | 0.62 |
| 20 | 3.14 | 0.27 | 0.31 | 0.62 |
| 21 | 3.85 | 0.26 | 0.31 | 0.63 |
| 22 | 4.40 | 0.26 | 0.30 | 0.62 |
| 23 | 4.87 | 0.26 | 0.31 | 0.62 |
| 24 | 5.30 | 0.27 | 0.30 | 0.62 |
| 25 | 5.58 | 0.26 | 0.31 | 0.62 |
| 26 | 5.72 | 0.27 | 0.31 | 0.62 |
| 27 | 5.74 | 0.26 | 0.30 | 0.62 |
| 28 | 5.74 | 0.26 | 0.31 | 0.62 |
| 29 | 5.75 | 0.26 | 0.31 | 0.62 |
| 30 | 5.75 | 0.27 | 0.32 | 0.62 |
| 31 | 5.75 | 0.26 | 0.31 | 0.62 |
| 32 | 5.75 | 0.27 | 0.31 | 0.62 |
| 33 | 5.74 | 0.27 | 0.31 | 0.62 |
| 34 | 5.74 | 0.26 | 0.30 | 0.62 |
| 35 | 5.74 | 0.26 | 0.31 | 0.62 |
| 36 | 5.74 | 0.27 | 0.30 | 0.62 |
| 37 | 5.73 | 0.27 | 0.30 | 0.62 |
| 38 | 5.73 | 0.27 | 0.30 | 0.62 |
| 39 | 5.73 | 0.27 | 0.29 | 0.62 |
| 40 | 5.73 | 0.26 | 0.30 | 0.62 |
| 41 | 5.73 | 0.26 | 0.30 | 0.62 |
| 42 | 5.72 | 0.26 | 0.30 | 0.62 |
| 43 | 5.73 | 0.27 | 0.30 | 0.62 |
| 44 | 5.72 | 0.26 | 0.30 | 0.62 |
| 45 | 5.72 | 0.27 | 0.31 | 0.62 |
| 46 | 5.72 | 0.26 | 0.07 | 0.27 |
| 47 | 5.55 | 0.27 | 0.00 | 0.00 |
| 48 | 5.24 | 0.01 | 0.00 | 0.00 |
| 49 | 4.98 | 0.00 | 0.00 | 0.00 |
| 50 | 4.74 | 0.00 | 0.00 | 0.00 |
| 51 | 4.49 | -0.01 | 0.00 | 0.00 |
| 52 | 4.25 | -0.01 | 0.01 | 0.00 |
| 53 | 3.99 | -0.01 | 0.00 | 0.00 |
| 54 | 3.76 | 0.00 | 0.00 | 0.00 |
| 55 | 3.53 | 0.00 | 0.00 | 0.00 |
| 56 | 3.29 | 0.00 | 0.00 | 0.00 |
| 57 | 3.07 | -0.01 | 0.00 | 0.00 |
| 58 | 2.86 | 0.00 | 0.00 | 0.00 |
| 59 | 2.64 | 0.00 | 0.00 | 0.00 |

FIG. 19

TABLE I part 2

| SECONDS | PRESSURE—INCHES OF WATER | | | |
|---|---|---|---|---|
| | present invention | ULTRATRIM | PAMPERS PREM | PCT 02/34184 A1 |
| 60 | 2.45 | 0.00 | 0.00 | 0.00 |
| 61 | 2.29 | −0.01 | 0.00 | 0.00 |
| 62 | 2.13 | 0.00 | 0.01 | −0.01 |
| 63 | 1.98 | 0.00 | 0.00 | 0.00 |
| 64 | 1.85 | 0.00 | 0.00 | 0.00 |
| 65 | 1.71 | 0.00 | 0.00 | 0.00 |
| 66 | 1.60 | 0.00 | 0.01 | 0.00 |
| 67 | 1.49 | 0.00 | 0.01 | 0.00 |
| 68 | 1.39 | 0.00 | 0.00 | 0.00 |
| 69 | 1.28 | 0.00 | 0.01 | −0.01 |
| 70 | 1.20 | −0.01 | 0.00 | 0.00 |
| 71 | 1.10 | 0.00 | 0.01 | 0.00 |
| 72 | 1.01 | 0.00 | 0.00 | 0.00 |
| 73 | 0.93 | −0.01 | 0.01 | 0.00 |
| 74 | 0.86 | 0.00 | 0.00 | 0.00 |
| 75 | 0.79 | 0.00 | 0.01 | −0.01 |
| 76 | 0.73 | 0.00 | 0.01 | 0.00 |
| 77 | 0.67 | 0.00 | 0.00 | −0.01 |
| 78 | 0.61 | 0.00 | 0.01 | 0.00 |
| 79 | 0.57 | 0.00 | 0.00 | 0.00 |
| 80 | 0.52 | −0.01 | 0.00 | −0.01 |
| 81 | 0.48 | 0.00 | 0.00 | 0.00 |
| 82 | 0.44 | −0.01 | 0.00 | 0.00 |
| 83 | 0.41 | 0.00 | 0.00 | 0.00 |
| 84 | 0.37 | 0.00 | 0.00 | 0.00 |
| 85 | 0.34 | 0.00 | 0.00 | 0.00 |
| 86 | 0.31 | 0.00 | 0.00 | 0.00 |
| 87 | 0.28 | 0.00 | 0.00 | 0.00 |
| 88 | 0.26 | 0.00 | 0.00 | −0.01 |
| 89 | 0.24 | 0.00 | 0.00 | 0.00 |
| 90 | 0.22 | 0.00 | 0.01 | 0.00 |
| 91 | 0.20 | 0.00 | 0.01 | 0.00 |
| 92 | 0.18 | −0.01 | 0.00 | 0.00 |
| 93 | 0.17 | 0.00 | 0.00 | 0.00 |
| 94 | 0.16 | 0.00 | 0.00 | 0.00 |
| 95 | 0.15 | 0.00 | 0.00 | 0.00 |
| 96 | 0.14 | 0.00 | 0.00 | −0.01 |
| 97 | 0.13 | 0.00 | 0.00 | −0.01 |
| 98 | 0.12 | 0.00 | 0.00 | 0.00 |
| 99 | 0.11 | 0.00 | 0.00 | 0.00 |
| 100 | 0.10 | −0.01 | 0.01 | 0.00 |

FIG. 20

DISPOSABLE LEAK-PROOF CONTAINMENT GARMENT

BACKGROUND OF THE INVENTION

Known personal care products, and especially incontinence undergarments and other items designed to absorb bodily fluids, typically are made with a top sheet material (also referred to as a cover sheet or liner), an absorbent core, or pad, and a liquid impervious back sheet. Some may also have a surge layer or other specialized layers between the top sheet and absorbent core. Absorption of fluid, comfort, and avoidance of leakage are the functions desired.

An ideal incontinence product, such as the personal care products discussed herein in conjunction with the present invention, would have no leakage and deliver comfort and discretion to the user. Current personal care products may have relatively high leakage and thus offer only modest protection to the consumer. Past product design has generally focused on three key causes of leakage: fluid does not absorb into the absorbent, fluid is absorbed into the absorbent but subsequently leaves it, or fluid never contacts the absorbent.

The specific reasons for leakage have been expressed further in terms of definitive mechanisms. A product, for instance, may not have suitable absorption due to localized saturation of the absorbent or insufficient area provided for fluid to contact the absorbent. The absorbent may not have a suitable driving force for absorption because its structures do not have the right balance of permeability and capillarity. The interfiber spaces may be fully or partially full of fluid. Fluid may contact the absorbent pad and run-off. The fluid may be too viscous or the pores or interfiber spaces are not large enough to allow fluid to pass through a surge layer to a subjacent absorbent layer.

In the past, the focus of the art has been on absorbency of the products. Liquid uptake rate and liquid volume capability of absorbent materials have in the past been the key considerations in providing an adequate time of retention. Thus, personal care product design has typically heretofore focused on the absorbent materials and their arrangement and concentration because leakage was considered to be a shortcoming of the functions of the absorbent materials, including the intake, distribution, retention and transfer rates, as well as shaping and conformability, of the absorbent materials.

Good fluid intake has been considered necessary in past garment construction. Intake includes the initial absorption of fluid into a dry product as well as the continued uptake of that fluid into the absorbent structure. Development of superior intake systems requires much effort and an understanding of environmental conditions including the nature of the fluid and its discharge. Developing functional intake structures requires an understanding of material characteristics and their interaction with the fluid as components and systems of components including interfaces and product design. Past product design efforts have included the arrangement and geometric design of material components and their interaction with the body and fluid.

Past product design efforts have also focused on the initial intake of bodily fluids into an absorbent article as a function of the characteristics of the liner or topsheet material and the upper absorbent layer. It has been recognized that the intake of bodily fluid into these materials is a function of the material characteristics including the ratio of void volume to fiber surface area, fiber orientation and fiber surface wettability. These intrinsic material characteristics can specifically define the more familiar material properties of permeability, capillarity and fiber wettability which can be calculated and measured by techniques well known in the art. Much effort has therefore been put into finding suitable intermediate layer and absorbent core matches for the characteristics of the liner to permit fluid communication and transfer. The task may be especially complicated considering the variation in liquid and solid flow rate, viscosity, location, surface tension, etc., from user to user and as these factors change for a user depending on the time of day.

As is known in the art, incontinence products such as diapers or other absorbent garments are often constructed from multiple layers of materials with each layer having a specialized function. For example, two common layers are the surge layer, specialized for the rapid uptake and distribution of bodily fluids away from the point of insult to the product and the absorbent layer which is specialized to hold and retain a high volume, or load, of liquid. However, the construction of garments with specialized layers, which may be functionally very efficient, may also lead to escalating product costs due to the expense of making and placing the multiple layers together in a garment. Thus, it is further desirable that the fluid handling, or distribution, layer and the fluid absorbent, or retention, layer be easily manufactured and incorporated into a personal care product in an economical fashion.

In each of the three key causes of leakage, time for absorption plays a critical role. A reason so much effort and expense has been spent on fluid distribution and absorption mechanisms of present personal care products is because the typical elasticized margin area of, e.g., a personal care garment, is leaky. Typically a marginal area is created with an application of pretensioned elastics which then contract, causing the marginal area of the garment to gather or shirr, creating a leaky seal against the body of the wearer. There remains a need for a personal care product that is able to contain body exudates in such a way as to keep the wearer protected from fluid being expressed out of the absorbent article over the amount of time necessary to allow complete absorption of bodily fluids, thus creating a "leakproof" garment structure.

Further, the known disposable or limited use garments; even when of a shaped or three dimensional design; are manufactured from flat materials such that when the garment is subsequently placed on the body, compromises of the fit between the marginal areas of the garment and the true body shape of the wearer provide avenues for leakage to the outside of the garment. This compromise of fit also affects the absorption and protection functions of the garment because the garment will tend to shift in relation to the body of the wearer when the wearer moves, affecting intended absorbent material placement and disrupting marginal seal placements against the body.

Thus, there further remains a need in the art to focus on exudate retention capability for incontinence garments, including a leakproof containment system, in order to lessen the burden on the uptake and absorbent materials of such garments.

SUMMARY OF THE INVENTION

The present invention more closely focuses on the barrier and containment functions of the personal care product in order that exudates do not leave the confines of the garment, whether exudate fluid contacts the absorbents of the garment or not. Special attention is thus given to the overall form of the garment and to the sealing of marginal areas, such as the waist and leg marginal areas. A personal care product according to one aspect of the present invention is provided with a containment shell made in a substantially humanoid form closely modeling true to life contours and three-dimensional aspects of the human form. Marginal seal areas of the product are most desirably formed from an elastic liquid-barrier material rather than having a pretensioned elastic material added thereto. The placement of tensioned elastics in past product design has been considered problematic. A product according to the present invention helps alleviate such problems by being formed initially, at least in part, of untensioned elastic or expandable materials. In some aspects of the invention it is desirable that the entire containment shell of the product be formed from an elastic, liquid barrier, material.

According to certain aspects of the present invention, a disposable, leakproof incontinence garment is formed from a liquid-impermeable shell. The garment may have non-prestressed elastic torso and appendage marginal seal areas at its openings to avoid the typical gathering, or shirring, of elastic margins common on current garments. The elastic margins are designed to conformably surround the torso and appendages of the wearer and form a tensioned and liquid tight seal against the skin of the wearer when donned. By forming liquid tight seals against the body of the wearer, the garment is favorably constructed to lessen the burden on, and utilize the full capability of, any absorbent structures placed within the shell. In aspects where the majority of the shell is elastic or expandable, the garment will shift very little when the wearer moves, leading to further efficacy of the containment and absorbent functions.

The garment may be made in any of a number of manners dependant upon the material selected for the shell. Aspects of the invention embodiments may include materials such as latex, elastomeric polymers, absorbent foams, nonwoven/film laminates, or the like. The chosen material may be selected to be breathable while retaining the liquid barrier function.

Methods of making the garment will generally be suited to the formation of a three-dimensional containment shell of humanoid shape, desirably of a size and shape designed to substantially conformably fit the wearer shape, and especially fitting closely at the marginal, e.g., waist and appendage, boundaries of the garment in order to aid in the formation of a leakproof garment with liquid tight seals at the margins of the garment. Such methods may include casting, such as solvent casting of polymers onto figured forms, dipping of forms into liquid phase shell material such as a latex, spraying or wrapping the shell material, injection or press molding, vacuum forming, etc., for forming onto a humanoid molding form or modified humanoid molding form, whether positive or negative, in conformance with the shape of intended wearers. Biometric data is considered to be sufficiently well established to provide a range of sizes for molds, and hence garments, of the present invention, necessary to accommodate the majority of wearers. The shape of the completed garment shell may include pouched areas for the containment and storage of exudate rather than being designed to be 100% conformal to the body. Such garments will still be considered to be shaped in substantial conformance with a human body shape according to the present invention.

In some aspects of the invention the garment may utilize differing amounts or types of materials within a single functional layer, such as having selected regions of thinner or thicker material, or materials of different elastic modulus, with preference being given to placing materials at the waist and appendage margins which allow for good liquid sealing without producing red marks on the wearer. Different amounts or types of materials may also be utilized within a garment to provide easier expansion of the garment in selected areas to make pockets for exudate containment. In some aspects, the central area of the garment may have a higher elastic modulus than the appendages to maintain the form fitting aspects of the garment. In some aspects, additional layers of materials may be added at key locations of the garment to increase the sealing capabilities of the gaskets or restrict the expansion of the body of the product.

The shell may be made unitary or have one or more seams and may, if desired, have the marginal areas reinforced with an additional application of elastic materials.

BRIEF DESCRIPTION OF THE DRAWINGS

These and other aspects and features of this invention will be better understood from the following detailed description taken in conjunction with the drawings, wherein:

FIGS. 19-20 represent the first and second pages, respectively, of Table 1, which is a two page table detailing the pressure data of FIG. 17.

DEFINITIONS

Figure 1:
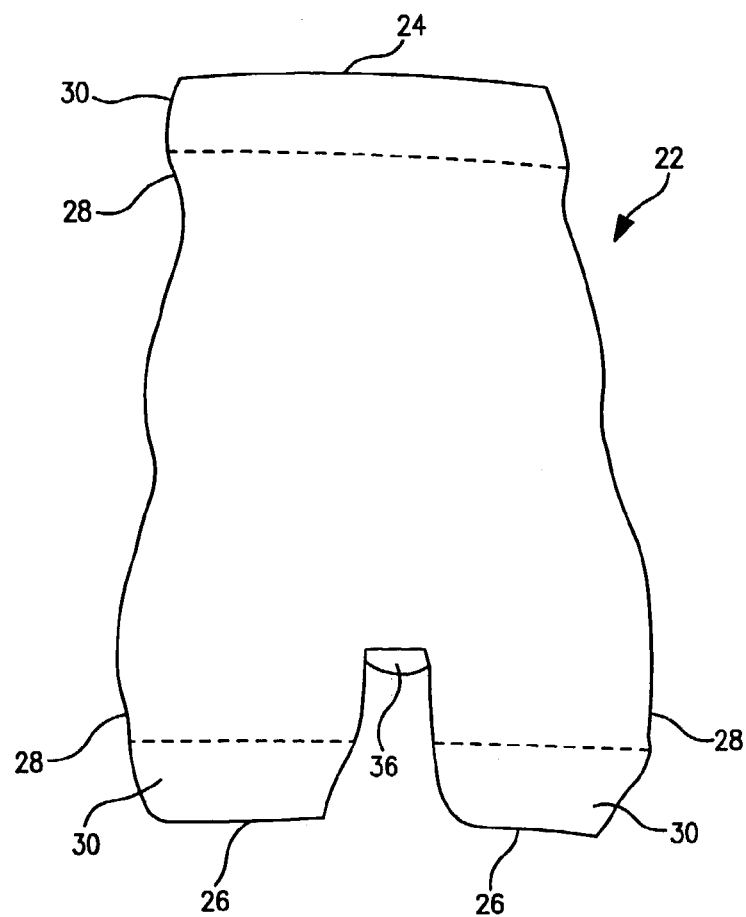
FIG. 1 illustrates a front view of an exemplary embodiment of a containment shell.

As used herein, the terms "disposable" and "limited use" mean a product designed to be discarded after a single or limited number of uses. Such products are thus typically light in weight and made with economical materials according to the present invention.

As used herein, the terms "elastic" and "elastomeric" when referring to a fiber, film or fabric mean a material which upon application of a biasing force, is stretchable and which will recover at least 50 percent of its elongation upon release of the stretching, biasing force.

"Expandable", as used herein, means a fabric which does not necessarily recover to the extent of being elastic, but which will expand and may maintain some contact against the skin of the wearer.

A "layer" is defined as a generally recognizable combination of similar material types or function existing in the same plane.

"Leakproof", and "substantially liquid tight" as used herein, mean the ability to maintain substantially no leakage of a gas against a rise in gas pressure sufficient to visibly increase a volume of space between the containment shell, or garment, and the wearer, or a mannequin representing a wearer; or maintain a gas pressure within the garment above atmosphere during pressure decay conditions after the rise in gas pressure, over a period of at least about 5 seconds. In the case of absorbent garments, "leakproof" may further refer to a product that is able to contain body exudates in such a way as to keep fluid from being expressed out of the boundaries of the absorbent article over that amount of time necessary to allow complete absorption of bodily fluids within the absorbent material.

As used herein the term "microfibers" means small diameter fibers having an average diameter not greater than about 75 microns (μm), for example, having an average diameter of from about 0.5 microns (μm) to about 50 microns (μm), or more particularly, microfibers may have an average diameter of from about 2 microns (μm) to about 40 microns (μm). Another frequently used expression of fiber diameter is denier, which is defined as grams per 9000 meters of a fiber and may be calculated as fiber diameter in microns (μm) squared, multiplied by the density in grams/cc, multiplied by 0.00707. A lower denier indicates a finer fiber and a higher denier indicates a thicker or heavier fiber. For example, the diameter of a polypropylene fiber given as 15 microns (μm) may be converted to denier by squaring, multiplying the result by 0.89 g/cc and multiplying by 0.00707. Thus, a 15 micron (μm) polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

"Meltblown fiber" refers to fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface.

"Nonwoven" refers to webs and layers of material having a structure of individual fibers or filaments which are interlaid, but not in an identifiable manner as in a knitted fabric. The terms "fiber" and "filament" may be used interchangeably herein. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and fiber diameters are usually expressed in microns. (Note that to convert from osy to gsm, multiply osy by 33.91.)

"Personal care products" shall include: absorbent articles used to absorb or contain any fluid including human body fluids, such as diapers, adult incontinence garments, training pants, absorbent swim pants, feminine care products, hygienic wipes, absorbent pads and the like; disposable apparel for institutional, industrial and consumer use; disposable health care products that are not intended to be cleaned for reuse, such as caps, gowns, foot wear, masks, drapes, wraps, covers, and the like; that are at least partially disposable.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as taught, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al. Spunbond fibers are quenched and generally not tacky when they are deposited onto a collecting surface. Spunbond fibers are generally continuous and often have average deniers larger than about 0.3, more particularly, between about 0.6 and 10.

"Substantial conformance with a human body shape" as referred to herein means that the shape of the garment is distinctly humanoid in three dimensional curve and contour when a positive pressure differential exists with the inside of the garment being at higher pressure than the outside of the garment.

Words of degree, such as "about", "substantially", and the like are used herein in the sense of "at, or nearly at, when given the design, manufacturing and material tolerances inherent in the stated circumstances" and are used to prevent the unscrupulous infringer from unfairly taking advantage of the invention disclosure where exact or absolute words or dimensions are stated as an aid to understanding the invention.

These terms may be defined with additional language in the remaining portions of the specification.

DESCRIPTION OF PREFERRED EMBODIMENTS

The various aspects and embodiments of the invention will be described in the context of disposable personal care products, and more particularly referred to, without limitation and by way of illustration only, as a disposable incontinence garment. It is, however, readily apparent that the present invention could also be employed to produce other products or garments, such as feminine care articles, medical garments or wraps, and other disposable garments. Typically, the disposable garments are intended for one-time or limited use, meaning they are not intended to be laundered or otherwise cleaned for reuse. A disposable diaper, for example, is discarded after it has become soiled by the wearer.

Referring to FIG. 1, there is seen a front view of a containment shell 22. The containment shell 22 is illustrated in this aspect of the invention as a pant-like garment with a unitary unseamed shell made in substantial conformance with a human body shape. As will be understood, the containment shell 22 will include an inside, or body side, surface and an outside surface. In FIG. 1, the containment shell 22 includes marginal seal areas of a non-prestressed elastic material including a torso margin 24 and appendage margins 26, designed for a waist opening and leg openings, respectively.

The containment shell 22 may have non-prestressed elastic torso and appendage margins at the openings thereof to avoid the typical gathering, or shirring, of elastic margins common on current garments. The gaskets, or seals, formed at the garment opening margins are most desirably elastic.

The elastic margins, or opening areas, are designed to conformably surround at least a portion of the torso and appendages of the wearer and form a tensioned and liquid tight seal against the skin of the wearer when donned. The margins, or marginal seal areas, 24, 26 may be sized to provide the conforming seal through either of a nominally straight portion 28 having proper sizing for a distinct range of body measurements or may be constructed with flange areas 30 of distinctly reduced or descending diameters over a flange area length of, e.g., about two inches, in order to insure a close fit of the marginal seal areas 24, 26 to a wider range of body sizes.

It is presently considered desirable to have the circumferences of the flange areas measure from at least ten percent to about seventy percent less than the true-to-life dimensions of the humanoid form in order to force the expandable or elastic material to stretch to make seal when the garment is in use. The elastic materials could be any suitable elastic, including but not limited to: polyurethane, styrenic block copolymers, such as KRATON commercial elastomers from Kraton Polymers of Houston, Tex.; polyether ester, such as HYTREL from E. I. Du Pont De Nemours & Company Corporation Wilmington, Del.; polyether amide, such as PEBAX, from Atochem Corporation, France; and elastic metallocene materials, such as AFFINITY, from Dow Chemical, Midland, Mich. Flange areas 30 could be made of material thicker than the rest of the shell, made of a different material, or have an additional material added to make an effective seal at the flanged or nonflanged marginal seal areas. Generally, it is envisioned that the shell, and all other layers of the garment, excluding absorbent structures, will have a basis weight between about 0.1 to about 20.0 osy.

Figure 2:
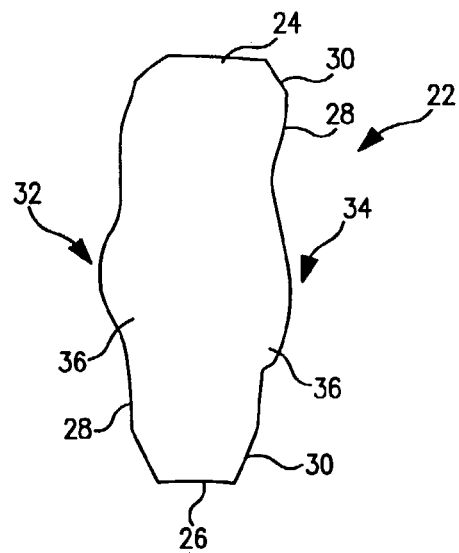
FIG. 2 is a side view of the containment shell of FIG. 1.

As more clearly seen in FIG. 2, the exemplary containment shell 22 further includes a ventral crotch area 32 and a dorsal crotch area 34. While designed to conformably fit the majority of body area which it will surround when donned by the wearer, the containment shell 22 may further have one or more pouch areas 36 that are designed to not conformably surround at least one of a torso and an appendage of the wearer, but are rather made larger than the true-to-life dimensions of the humanoid form in order to provide exudate storage areas within the donned garment. In some aspects of the invention the majority of the containment shell outside of the marginal seal areas may be made larger than the true-to-life dimensions of the humanoid form to hold the exudate while only the seal areas are tight.

Figure 3:
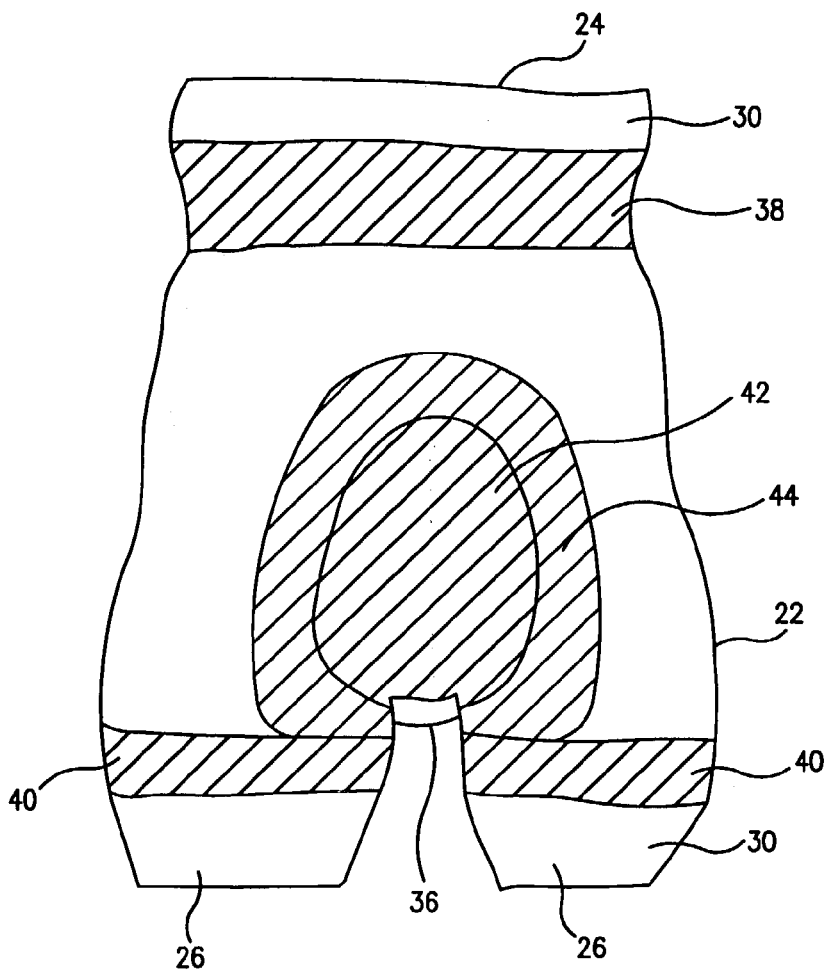
FIG. 3 illustrates a front view of an exemplary embodiment of a containment shell with absorbent material applied therein.
Figure 4:
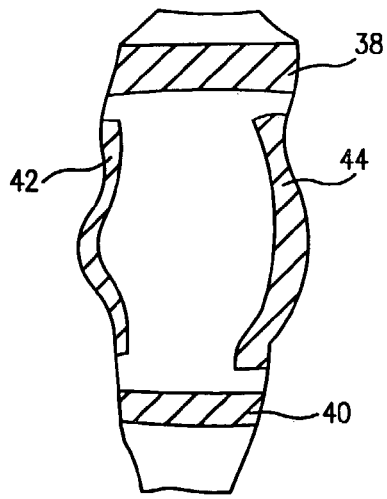
FIG. 4 is a side view of the containment shell of FIG. 3.

Referring to FIGS. 3 and 4, there are seen views of the containment shell 22 illustrated as a pant-like garment having absorbent materials within a unitary unseamed shell made in accordance with the shape and contours of the human form. The absorbent materials include waist area absorbents 38 and leg area absorbents 40 applied in bands on the body side, or surface, of the containment shell 22 to encircle the wearer. Additional absorbent materials include a ventral crotch area absorbent pad 42 and a dorsal crotch area absorbent pad 44. The absorbent materials described herein may be attached to the containment shell 22, integral therewith, or may be designed to be inserted into the containment shell 22, or donned separately and worn next to the skin and then overlaid by the containment shell 22. The absorbent materials are envisioned to be shaped substantially in conformance with the body shape, but may also be made substantially flat and yet flexible enough to achieve conformance to the body when held in place on, or by, the containment shell 22.

Figure 9:
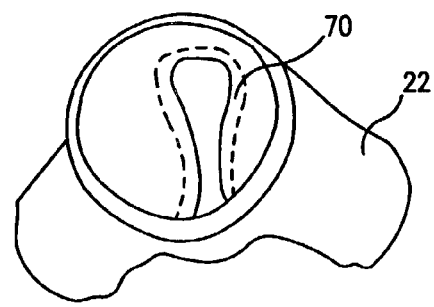
FIGS. 9 and 10 illustrate top and side views, respectively, of a containment shell embodiment having a pocket formed therein for retention of an absorbent.
Figure 10:
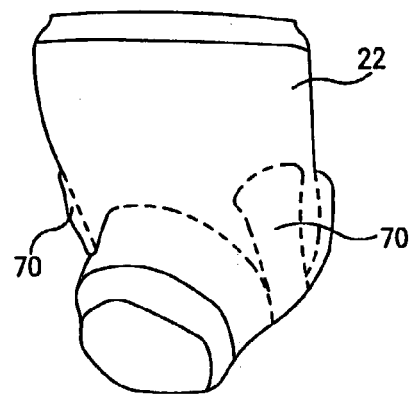
Figure 11:
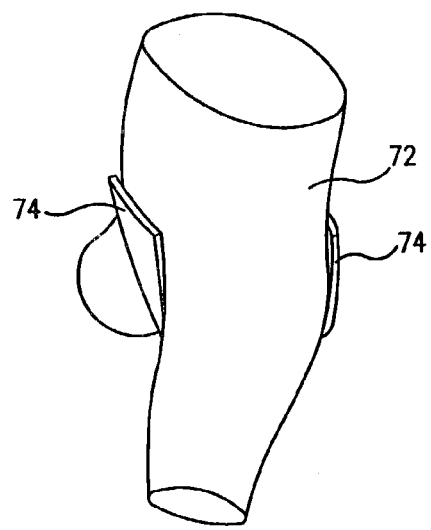
FIG. 11 illustrates a humanoid molding form suitable for the making of an embodiment according to FIGS. 9 and 10.

In the embodiment of FIG. 9 and FIG. 10, the containment shell 22 further comprises an integral pocket 70, here shown as comprising a contiguous flap, for surrounding an edge of an absorbent insert (not shown) and holding the absorbent insert in the so-called "target area" most likely to receive insult from bodily exudates. The humanoid molding form 72, as seen in FIG. 11, shows how the flap may be integrally molded with the containment shell by providing the mold 72 with a relief form 74 for molding the pocket 70 in one operation. The pocket 70 may also be seen to provide a pouch area not strictly conforming to the body to provide area for the storage of free liquids within the garment.

Figure 5:
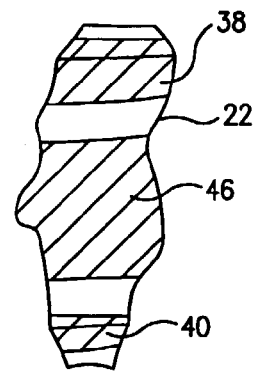
FIG. 5 is side view illustrating an alternative embodiment of the containment shell of FIG. 4.
Figure 6:
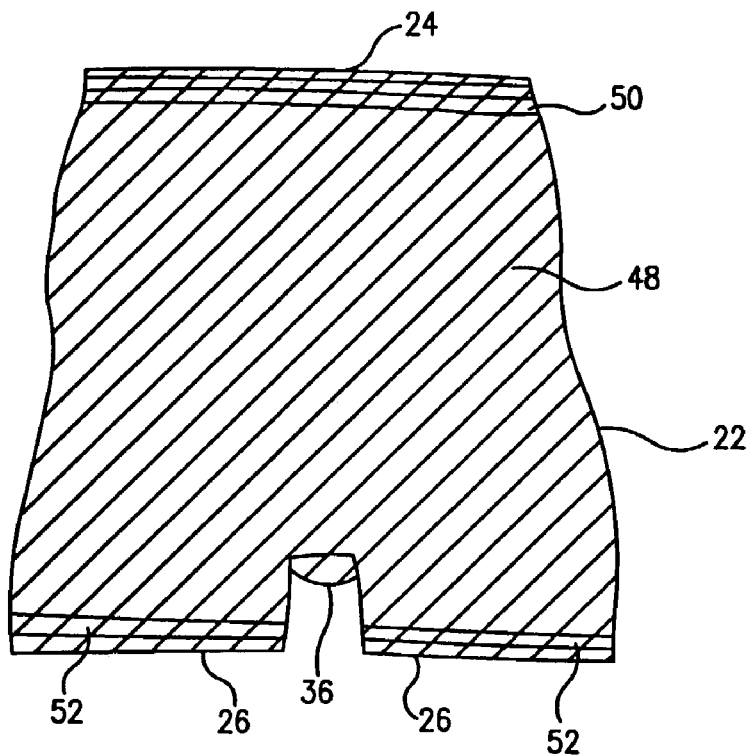
FIG. 6 illustrates a front view of an alternative embodiment of a containment shell.

In the embodiment of FIG. 5, a crotch area absorbent 46 is shown as applied over the entire circumference of the body side of the containment shell 22 in the crotch area so as to completely surround the wearer. Further absorbent materials may include waist area absorbents 38 and leg area absorbents 40 applied in bands on the body side, or surface, of the containment shell 22 to encircle the wearer, as per the embodiments of FIGS. 3 and 4. In the embodiment of FIG. 6, an absorbent layer 48 is shown as applied over the entire body side surface of the containment shell 22 so as to completely surround the wearer. The embodiment of FIG. 6, although otherwise similar to the previously detailed embodiments of containment shell 22, lacks flange areas at the marginal seal areas 24, 26 of the containment shell 22 and instead has additional elastic members 50, 52 applied about the circumferences of the marginal seal areas 24, 26, respectively, in order to reinforce the seal against the flesh of the wearer in such areas. It will be appreciated that such reinforcing elastic members 50, 52 may be applied to embodiments with or without flange areas 30 (FIG. 1). In any of the embodiments herein it will be appreciated that no gathering or shirring of the margins is desired to take place due to application of pretensioned elastic members at the margins.

Figure 12:
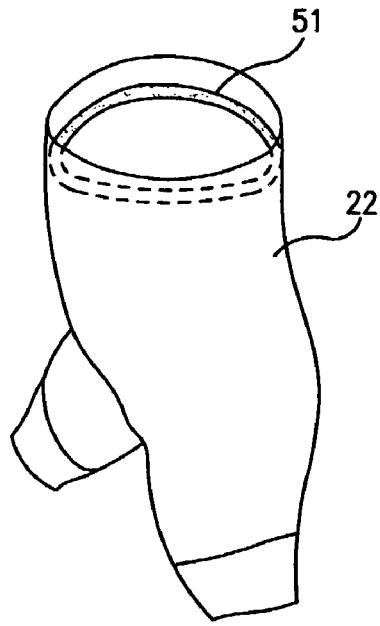
FIG. 12 illustrates a upper left perspective view of a containment shell embodiment having a resilient non-absorbent waist gasket therein.

The most difficult area of the containment shell 22 to seal against fluid transmission may be the back waistband area due to backbone protrusion and indentations lateral thereto of the wearer. Therefore, a compressible, resilient, non-absorbent gasket 51, more readily conformable to the protrusions and indentations of the backbone area maybe added inside of the waistband, and especially at the back, or dorsal, waistband area to further provide a conformable seal in this area. Referencing FIG. 12, the gasket 51 is preferably continuous around the waist to provide a re-enforcement of sealing tension and may take the place of a reinforcement elastic waistband 50 (FIG. 6). The gasket 51 may alternatively be a site specific enhancement of material. For example, in one aspect of the invention further described below, the containment shell 22 may be comprised substantially of an exterior-skinned absorbent foam. In this case, the foam may be built up in the spinal area, as initially molded, to form an integral gasket and then have a non-absorbent skin applied thereto. The gasket 51 may be a compressible, elastic, closed-cell foam such as RESILITEX, available commercially from Foamex International Inc., of Linwood, Penn., or be made from other known polyurethane foams or the like. The gasket 51 may be of a variety of shapes such as, e.g., a parallelepiped one inch wide and one half to three-eights inch thick, or it may be round, half-round, pillowed, or accordion pleated. Alternatively, the gasket 51 may be a fluid inflatable band or the like. It will be appreciated that the described gasketing technique may be used at any desired marginal area of a personal care product.

Figures 7, 8:
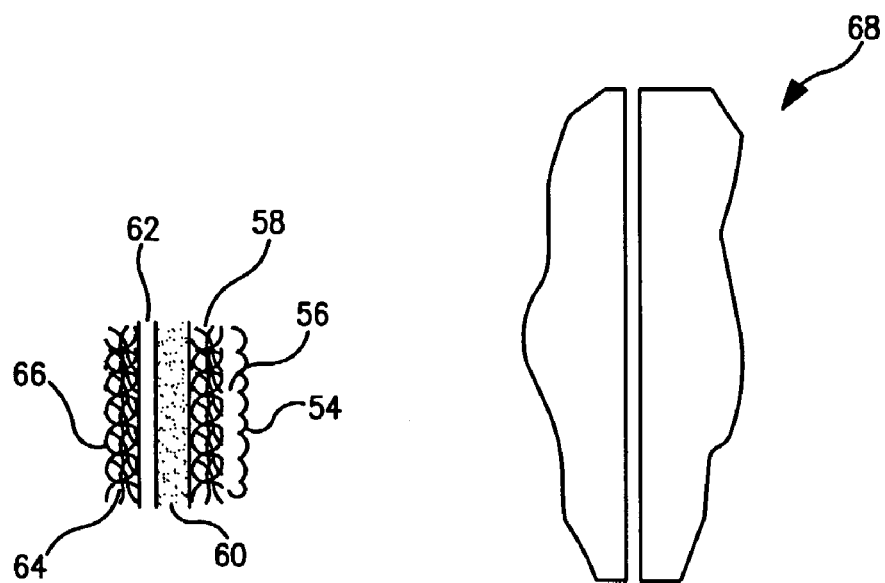
FIG. 7 is a cross section of one embodiment of the containment shell material illustrating exemplary layers thereof.
FIG. 8 illustrates a two-piece torso humanoid molding form of the positive type which may be utilized in making a containment shell according to one aspect of the invention.

Referencing FIG. 7, a cross section of garment material layers suitable for one aspect of the present invention is provided. At the body side, or interior surface, 54 of the garment is a liner material 56 having cloth-like feel. The material may be a nonwoven spunbond or the like such as is known in the art and deemed suitable for its intended purposes within an embodiment of the present invention. It will be noted that the liner material should not restrict the expansion of the waist or leg opening seal areas. The liner material 56 may be elastic or extendable, in one or more directions, and be directly attached to the seal areas. The garment may have a non-extendable liner if the garment is designed so the liner is not attached to the marginal seal areas and otherwise does not inhibit the easy extension of the marginal seal areas. Subjacent to the liner material 56 layer is a surge layer 58 to aid in the uptake and distribution of exudate insults within the garment. The material may be any surge material composition and construction such as are known in the art and deemed suitable for its intended purposes within an embodiment of the present invention. The surge layer material 58 may, like other layers, be elastic or extendable, in one or more directions, if directly attached to the seal areas, or may be non-extendable if the layer is not attached to the seal areas and otherwise does not inhibit the extension or retraction of the seal areas.

Subjacent to the surge layer 58 is an absorbent layer 60 to provide primary absorption and retention of liquid within the garment. The material may be any number of known absorbent foams or a nonwoven web or pulp pad with superabsorbents, or any absorbent material composition and construction such as are known in the art and deemed suitable for its intended purposes within an embodiment of the present invention. Desirably, the absorbent layer may be elastic or expandable and will stretch in one or more directions.

The person having ordinary skill in the art will appreciate that a lesser amount of absorbents may be used within structures according to the present invention because the absorbents will have time to be more fully utilized owing to the fact that all liquid will be contained within the garment shell for a period of time sufficient to allow complete absorption. No excess of absorbents need be provided, thus presenting the possibility of material savings and a less complicated construction for the garment. It will be noted that such aspects of the invention may reduce the need for one or-more of the various layers shown in FIG. 7.

Subjacent the absorbent layer 60 is an elastic, liquid-impervious film layer 62 which may represent the basic construction and material of the containment shell 22. The elastic, liquid-impervious film layer 62 may be constructed from a variety of construction and material choices as mentioned above or as further known in the art or later developed and may include breathable materials which will pass water vapor but present a barrier to liquids. Some exemplary breathable, i.e., water vapor permeable, liquid barrier elastic films are described in U.S. Pat. No. 5,883,028, to Morman et al., issued Mar. 16, 1999, describing inherently breathable films; and U.S. Pat. No. 5,932,497 to Morman, et al., issued 3 Aug. 1999, describing microporous breathable films.

Adjacent the liquid impervious film layer 62 may be a facing material layer 64 to give the exterior surface 66 of the garment a more esthetic look and feel. The material may be any material composition and construction such as are known in the art and deemed suitable for its intended purposes within an embodiment of the present invention.

The liquid impervious film layer 62 and the facing material layer 64 may be provided in some instances as a single laminate which will be the first layer applied to a humanoid molding form in the garment forming process. Alternatively, the facing material layer 64 may be the residual parts of a release substance applied to the humanoid molding form prior to application of the liquid impervious film layer 62. It should be considered that economical construction techniques may require that all or several material layers be fusible under heat, pressure, or the like, or otherwise joined as an integral part of the construction process. Alternatively, all layers may be constructed into a single web and then formed against humanoid molding forms if desired. It should also be noted that where the entire garment is to be elastic it is important that all or several layers of the garment allow suitable expansion and contraction to accomplish the purposes of the present invention. As previously noted, each layer is desirably between about 0.1 and about 20.0 osy.

For example, the combination of the liquid impervious film layer 62 and the facing material layer 64, or various of the other layers, may comprise an elastomeric material such as a neck-bonded laminate (NBL) or stretch-bonded laminate (SBL) material. Methods of making such materials are well known to those skilled in the art and are described in U.S. Pat. No. 4,663,220 issued May 5, 1987 to Wisneski et al., U.S. Pat. No. 4,741,949 issued May 3, 1988 to Morman et al., U.S. Pat. No. 5,226,992 issued Jul. 13, 1993 to Morman, and European Patent Application No. EP 0 217 032 published on Apr. 8, 1987 in the names of Taylor et al. It is also contemplated that the elastic film layer 62, or other layers, might be expanded, such as with air pressure from inside a molding form, in order to arrange suitable ones of the above combinations of facings and elastic layers.

Conventionally, "stretch bonded" refers to an elastic member being bonded to another member while the elastic member is extended at least about 25 percent of its relaxed length. "Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered. Such a multilayer composite elastic material may be stretched to the extent that the nonelastic material gathered between the bond locations allows the elastic material to elongate. One type of stretch bonded laminate is disclosed, for example, by U.S. Pat. No. 4,720,415 to Vander Wielen et al., in which multiple layers of the same polymer produced from multiple banks of extruders are used. Other composite elastic materials are disclosed in U.S. Pat. No. 4,789,699 to Kieffer et al. and U.S. Pat. No. 4,781,966 to Taylor. Further reference will be had to U.S. Pat. Nos. 4,652,487 and 4,657,802 to Morman and 4,655,760 to Morman et al.

Conventionally, "neck bonded" refers to an elastic member being bonded to a non-elastic member while the non-elastic member is extended and necked. "Neck bonded laminate" refers to a composite material having at least two layers in which one layer is a necked, non-elastic layer and the other layer is an elastic layer. The layers are joined together when the non-elastic layer is in an extended and necked condition. Examples of neck-bonded laminates are such as those described in U.S. Pat. Nos. 5,226,992; 4,981,747; 4,965,122 and 5,336,545 to Morman.

Conventionally, "necked stretch bonded" refers to an elastic member being bonded to a non-elastic member while the non-elastic member is extended and necked and the elastic member is at least extended. "Necked stretch bonded laminate" refers to a composite material having at least two layers in which one layer is a necked, non-elastic layer and the other layer is a stretched, and sometimes necked, elastic layer. The layers are joined together when in their extended (and necked) conditions. Examples of necked stretch bonded laminates are described in U.S. Pat. Nos. 5,114,781 and 5,116,662 to Morman.

It will be appreciated by the person having ordinary skill in the art that some parts of the garment or containment shell that contact the seals could be elastic, i.e. with recovery, or just extendable, i.e. without recovery or insufficient recovery to be considered truly elastic. For example, the liner material 56 might be creped spunbond or a necked spunbond, or both, or an inherently extendable spunbond material such as a crimped bicomponent fiber nonwoven material. Other parts of the garment may be elastic, extendable, or non-extendable so long as they do not interfere with the extendibility or retraction of the elastic seals. Care should be taken in the placement of the above-discussed laminates that extendability of the laminate is in a direction or directions suitable for the design of a garment according to the present invention.

Referencing FIG. 8, there is shown a two-piece standard torso biomorphic, and particularly humanoid, molding form 68 of the positive type which may be utilized in making a containment shell according to one aspect of the invention. The halves may be independently used to form a front, or ventral, half of the garment and a back, or dorsal, half of the garment. Upon completion of both halves, the halves may be seamed together, such as by heat or adhesives, to create a leakproof garment. In this aspect of the present invention, the seam areas may be used as a convenient breaking point on the integrity of the garment in order to facilitate removal of the garment from the wearer. Alternatively, a one piece humanoid forming mold may be used. A mold may contain more than one humanoid form to allow the formation of more than one containment shell at a time in order to reduce trim waste from the process. The molds may be of positive or negative humanoid shapes, or both, in some applications such as press molding. The molding process is not intended to be limited herein to any one application or method but may utilize whatever system is found to be most convenient or economical to the manufacture of the garment.

Methods of making the containment garment will generally be suited to the formation of a three-dimensional humanoid shaped containment shell designed to fit the wearer shape. As discussed above, the garment may be constructed to fit closely, i.e., be tensioned, to the wearer over the entire surface of the garment or may include areas of more relaxed fit, i.e., less tensioned or untensioned, which then join to those areas of especially close fit located only at the marginal, e.g., waist and appendage, seal boundaries of the garment in order to form liquid tight seals.

Methods for construction of the containment shell may include casting, such as solvent casting of polymers, e.g., suitably solvated elastomers, onto figured forms. Solvent casting will often provide the advantages of very even film formation with minimal chance of openings in the shell and a low degree of orientation for the film. Methods for dipping of forms into liquid phase shell material, such as latex, as may be analogous to the making of gloves or the like, may also be used. Spraying of shell material onto the molding form may further be possible, dependent upon the materials used. Spraying may include the placement of thermoplastic microfibers or the like from known extrusion equipment with the fiber layer subsequently heat treated to provide additional integrity to the shell if desired or necessary. Also as a further example, meltblown polyurethane microfibers may be formed on the garment to make the outside surface of the product. It will be appreciated by the person having ordinary skill in the art that some garments according to the present invention with multiple layers are likely to be made "inside out" with the exterior layers formed closest to the humanoid shaped molding form and applied successively outward until application of the interior layer, at which time the product may be taken off the molding form and inverted for proper donning orientation.

In another aspect of the invention, the containment shell may be comprised substantially of an exterior-skinned absorbent foam. Such a shell may be a known absorbent foam, such as a polyurethane open celled foam, sprayed or otherwise applied onto a humanoid molding form and covered with an exterior layer of compatible liquid barrier film. One such suitable absorbent foam may be a surfactant treated hydrophilized polymeric foam material, also termed a "High Internal Phase Emulsion" absorbent foam, such as disclosed in U.S. Pat. No. 5,352,711, to DesMarais, herein incorporated by reference. The application of a liquid barrier layer may be accomplished by dipping the foam-covered mold into a liquid phase elastic block copolymer such as KRATON, or latex polyurethanes or latex silicone rubbers, or the like. It is envisioned that surface treatment of certain foams, such as by heat, chemical treatment, or the like, may also provide a liquid barrier without the need for additional layers or materials. It will be appreciated that the "exterior" liquid barrier layer may start as a layer closer to a molding form and later be reversed to become the exterior surface of the garment.

Injection or press molding, vacuum forming, etc., may be used for wrapping or forming pre-made webs of shell material, or entire garment material, onto or into a humanoid molding form or modified humanoid molding form, whether positive or negative, in substantial conformance with the shape of intended wearers. The shape of the modified humanoid molding forms may include pouched areas for the containment and storage of exudate within the shape of the shell rather than being designed to be 100% conformal to the body.

Figure 14:
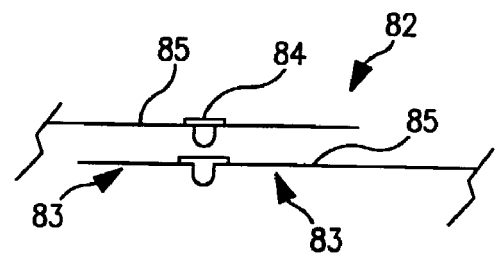
FIGS. 14-16 illustrate cutaway end views of various embodiments of side seams.
Figure 15:
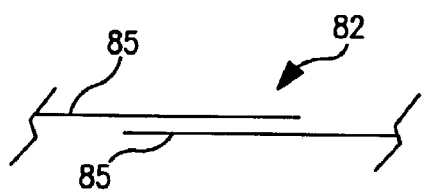
Figure 13:
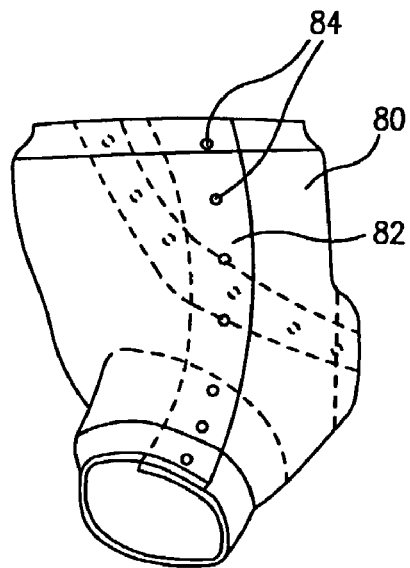
FIG. 13 illustrates a containment shell embodiment having side seams.
Figure 16:
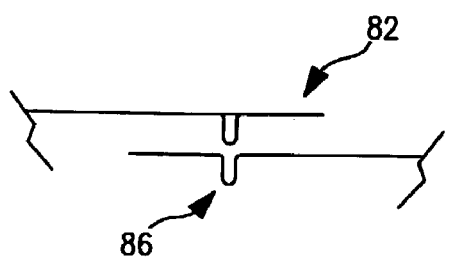

Referring to FIGS. 13-16, in another aspect of the invention, an embodiment of the containment shell 80 may be seamed, such as by side seams 82 on the right and left legs of the shell in the case of a pant-like garment. As shown in FIG. 13 and FIG. 14, the seam 82 comprises an overlap 83 of containment shell material 85 reinforced by mechanical fasteners 84, in this case illustrated as snaps. It is desirable that the containment shell material 85 in the seam 82 have a cohesive affinity for itself in order to properly seal the seam 82 from the passage of liquid. One such material may be a block co-polymer and polyethylene blend as disclosed in U.S. Pat. No. 6,261,278 to Chen et al. and taught as suitable for use as an adhesive member in a disposable incontinence garment. Tackifiers might also be used in the material 85 of the seam 82 in order to enhance the affinity of the overlapping materials 85. As seen in an alternative aspect of FIG. 15, if sufficient bond strength is available between materials 85 without mechanical fasteners, the seam 82 may be left without mechanical reinforcement. As seen in FIG. 16, the seam 82 may comprise an integrally molded resealable seam 86 of polymer-to-polymer tongue and groove construction analogous to those used on known resealable storage bags. Such seaming arrangements as, e.g. the polymer-to-polymer tongue and groove construction, are also contemplated to allow for the addition of independently provided gasketing materials which might be individually selected by the consumer and applied to waist and appendage margins of a basic containment shell or pant-like garment. It will further be appreciated that seam location of a personal care product may be placed according to the dictates of various designs. Various bonding, co-extrusion, or sectional molding techniques may be utilized singly or in combination to form a seam of distinct material from that of the other containment shell areas if necessary or desired.

Figure 17:
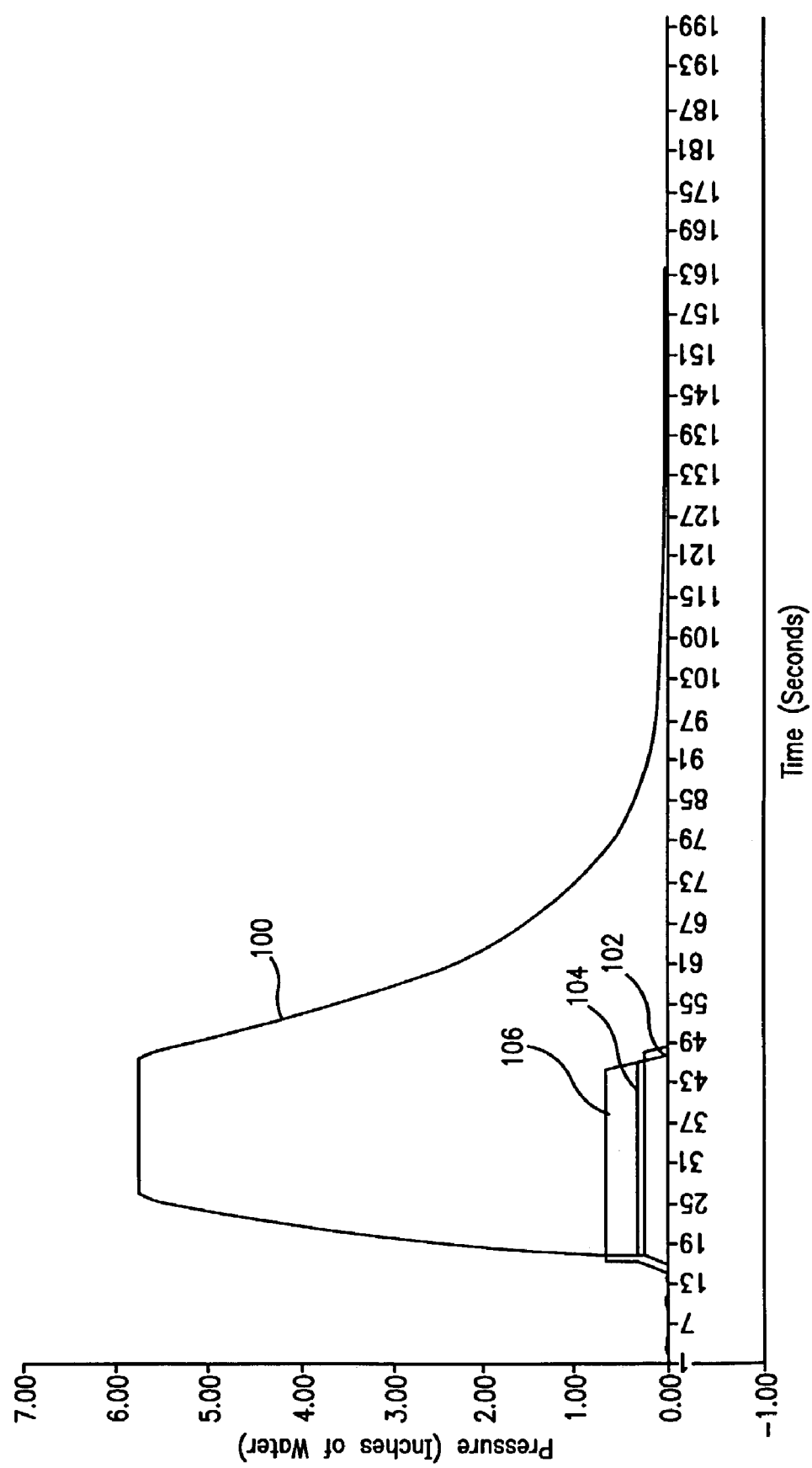
FIG. 17 illustrates the fluid-sealing and retention capabilities of a containment shell according to the present invention as compared to more conventional style diapers.

As seen in the graph of FIG. 17, and in FIGS. 19 and 20 (Table I), a containment shell according to aspects of the present invention presents greater fluid sealing and retention properties than three more conventional type diapers. The curves of the graph are a plot of time (X axis) versus gas pressure (above atmosphere) in inches of water (Y axis). Curve 100 represents the data for an unseamed latex containment shell of about 7.96 osy latex and 23.1 g total weight with margin gasketing similar to FIG. 1 of the present invention. Curve 102 represents data for a HUGGIES ULTRATRIM brand commercial diaper available from Kimberly-Clark Corporation in the November/December 2002 timeframe. Curve 104 represents data for a PAMPERS PREMIUM brand commercial diaper, UPC code 3700034820, available from Proctor & Gamble Corporation in the November/December 2002 timeframe. Curve 106 represents data for an expandable diaper made according to the teachings of PCT Publication WO 02/34184 A1, published May 2, 2002 in the names of Vukos, et al.

Figure 18:
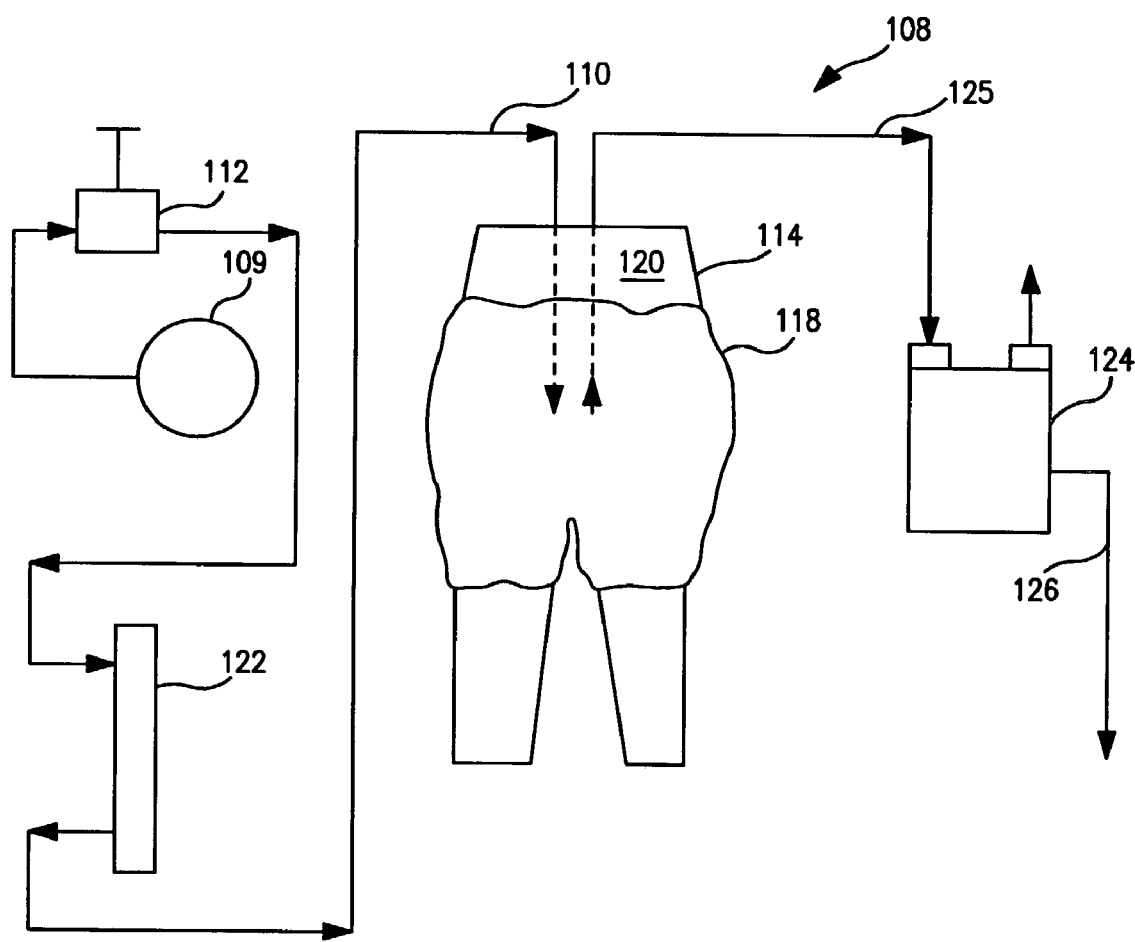
FIG. 18 illustrates the test set up used to determine the data according to FIG. 17.

FIG. 18 shows the fluid sealing and retention test set up 108. Air pressure 110 from an air supply 109 is adjusted by the air pressure regulator 112, to above the expected seal capacity of a containment shell of the present invention. The regulated fluid (air) enters the garment 118, through the female filling port of a test mannequin or "torso" such as Part No. CLARA MIDI-3MM, available from Courtray Consulting of Douai, France, which the garment has been placed on. A "soft" test mannequin 114, such as one having a vinyl chloride surface skin 120, is preferred for simulating the sealing effect of the garments on a human wearer. The air supply to the mannequin 114 is then set to a specified flow rate, of e.g., 19,622 ml/min., by the flow meter 122, e.g., a Cole Palmer Model No. 44-40. As the pressure begins to rise above atmosphere, the pressure transducer 124, connected by tubing 125 through the male filling port of the test mannequin, translates a pressure signal into an analog DC voltage signal 126 which is in direct proportion to the air pressure within the garment 118 (relative to the atmospheric reference). This DC voltage 126 can be used in a data collecting apparatus (not shown) such as a data logger, or computer device for data capture. In the graph of FIG. 17 and FIGS. 19-20 (Table I), air was applied by manually turning a valve after about 15 seconds, allowing air to enter the garment until the turn off of air input at about 45 seconds, i.e. an air flow cycle occurred between 15 and 45 seconds of the test. At 45 seconds the air input was turned off, i.e., a pressure decay condition was entered, and deflation/retention readings were taken out to 100 seconds. In the reported data, a larger sized step 4 mannequin was used as a torso mold for the containment shell of the reported example. A smaller, step 3 size soft (vinyl skinned) mannequin was used to place the example test garments on for pressure testing. Thus, a 6 mm wide rubber band surrounding the waist of the present invention test example at a tension of about 260 g at extention around the 45 cm waist circumference of the mannequin 114 was used to simulate the proper fitting of the larger sized containment shell on the smaller test mannequin. The leg gasketing was not considered necessary to reinforce despite the smaller size mannequin.

Curve 102 illustrates that a latex containment shell according to aspects of the present invention reached a pressure of 5.75 inches of water at 29 seconds during the air flow cycle and substantially retained this pressure through 47 seconds. At the air turn off point of about 45 seconds, or so called "pressure decay conditions" where maximum pressure had been reached and no further air was being put in, the exemplar of the present invention dropped in pressure of about 1 inch of water over each of the next 2 or 3 four-second intervals (4.74 inches of water at 50 seconds, 3.76 inches of water at 54 seconds, 2.86 inches of water at 58 seconds), gradually thereafter declining to 1.01 inches of water pressure at the 72 second mark and reaching 0.10 inches of water pressure at 100 seconds. The containment shell example of the present invention was actually inflated during the testing, expanding away from the mannequin form over substantially all but the gasket areas of the shell, thereby visibly distending the shell and increasing volume between the containment shell and the mannequin.

Curve 106 reached a high of 0.62 inches of water pressure at 17 seconds and retained that value during the air flow cycle before sharply dropping to zero pressure at 47 seconds. No visible inflation or distension of the expandable diaper type according to PCT Publication WO 02/34184 A1 away from the test mannequin was noted.

Curve 104 reached a high of 0.31-0.32 inches of water pressure at 17 seconds and retained that value (during the air flow cycle) before sharply dropping to near zero pressure at 46 seconds. No visible inflation or distension of the PAMPERS diaper type away from the test mannequin was noted.

Curve 102 reached a high of 0.26-0.27 inches of water pressure at 17 seconds and retained that value (during the air flow cycle) before sharply dropping to near zero pressure at 48 seconds. No visible inflation or distension of the HUGGIES diaper type away from the test mannequin was noted.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

What is claimed is:

1. A personal care incontinence product for a wearer, the personal care product having a body side and an outside, comprising:
   a unitary unseamed liquid-impermeable contoured shell comprising an absorbent foam applied over an entire circumference of the body side with a latex liquid barrier layer;
   the liquid-impermeable shell having an untensioned humanoid or modified humanoid molding form in substantial conformance with a human body shape to surround at least a portion of the wearer and form a seal against the wearer wherein the seal is constructed and arranged to maintain a pressure of gas contained within the garment above atmospheric pressure, over a period of at least about 5 seconds at pressure decay conditions;
   the liquid-impermeable shell having an elastic torso margin and elastic appendage margins at openings thereof which are devoid of gathering and shirring.

2. The personal care product of claim 1 wherein the personal care product comprises a liquid-impermeable elastomer shell solvent cast on the molding form.

3. The personal care product of claim 1 wherein the personal care product further comprises a discrete absorbent insert unattached to the liquid-impermeable shell.

4. The personal care product of claim 3 wherein the discrete absorbent insert comprises an extruded foam absorbent shaped in substantial conformance with the liquid-impermeable shell.

5. The disposable containment garment for a wearer according to claim 1, wherein the garment is able to be filled with a gas to a fluid pressure of 5.75 inches of water during an air flow cycle and thereafter being able to retain a pressure of at least 1.00 inches of water above atmosphere for about 27 seconds at pressure decay conditions.

6. The personal care product of claim 1 wherein the personal care product comprises a diaper.

7. The personal care product of claim 6 wherein the diaper is disposable.

8. The personal care product of claim 1 wherein the personal care product comprises economical materials.

9. The personal care product of claim 1 wherein the latex is selected from the group consisting of liquid phase elastic block copolymers, latex polyurethanes, latex silicone rubbers and combinations thereof.

10. The personal care product of claim 1 wherein the absorbent foam comprises polyurethane open celled foam.

11. The personal care product of claim 1 wherein the absorbent foam comprises a high internal phase emulsion.

12. A disposable containment garment for a wearer, the garment having a body side and an outside, comprising:
a unitary unseamed liquid-impermeable contoured shell comprising an absorbent foam applied over an entire circumference of the body side with a latex liquid barrier layer, and having a non-prestressed elastic torso margin and non-prestressed elastic appendage margins which are devoid of gathering and shining;
the liquid-impermeable shell having an untensioned humanoid or modified humanoid molding form in substantial conformance with a shape of the wearer; and
the elastic margins designed to conformably surround at least a portion of a torso and an appendage of the wearer and form a tensioned liquid seal against the skin of the wearer, wherein the seal is constructed and arranged to maintain a pressure of gas contained within the garment above atmospheric pressure, over a period of at least about 5 seconds at pressure decay conditions.

13. The disposable containment garment for a wearer according to claim 12, further comprising: the garment constructed from materials of a weight of about 0.1 osy to 20 osy, exclusive of any absorbent structures, so as to be economical for a single or limited use wearing.

14. The disposable containment garment for a wearer of claim 12 wherein the elastic margin designed to conformably surround at least a portion of a torso further comprises a compressible, resilient, non-absorbent gasket readily conformable to the protrusions and indentations of a backbone area of the wearer.

15. A disposable, leakproof, containment garment for a wearer, the garment having a body side and an outside, comprising:
a unitary-unseamed liquid-impermeable shell comprising an absorbent foam applied over an entire circumference of the body side with a latex liquid barrier layer, and having an untensioned three dimensional molding form including a non-prestressed elastic torso portion and non-prestressed elastic appendage-surrounding portions with margins through which a torso and appendage of the wearer may pass;
the margins being devoid of gathering and shirring and including flanges of reduced diameter from that of the torso and appendage-surrounding portions in order that the flanges may conformably surround the torso and appendage of the wearer and form a tensioned seal against the skin of the wearer, wherein the seal is constructed and arranged to maintain a pressure of gas contained within the garment above atmospheric pressure, over a period of at least about 5 seconds at pressure decay conditions.

16. The disposable, leakproof, containment garment for a wearer according to claim 15, further comprising:
the liquid-impermeable shell being manufactured in substantial conformance with a shape of the wearer.

17. The disposable, leakproof, containment garment for a wearer according to claim 16, further comprising:
at least one of a nonwoven layer, a breathable elastic layer, and an absorbent foam layer.

18. The disposable, leakproof, containment garment for a wearer according to claim 17, further comprising:
the liquid-impermeable shell further having pouch areas designed to not conformably surround at least one of a portion of a torso and a portion of an appendage of the wearer in order to provide exudate storage within the garment.

19. The disposable, leakproof, containment garment for a wearer of claim 18 wherein the elastic margin designed to conformably surround at least a portion of a torso further comprises a compressible, resilient, non-absorbent gasket readily conformable to the protrusions and indentations of a backbone area of the wearer.

20. A disposable containment garment for a wearer, the garment having a body side and an outside, comprising:
a unitary unseamed liquid-impermeable contoured shell with an elastic torso margin and elastic appendage margins which are devoid of gathering and shining;
the liquid-impermeable shell comprising an absorbent foam applied over an entire circumference of the body side with a latex liquid barrier layer, and having an untensioned humanoid or modified humanoid molding form in substantial conformance with a shape of the wearer;
the elastic margins being designed to conformably surround at least a portion of a torso and an appendage of the wearer and form a tensioned and a substantially liquid tight seal against the skin of the wearer;
the liquid tight seal being constructed and arranged to maintain substantially no leakage of a gas against a rise in fluid pressure above atmosphere during an air flow cycle and maintain a gas pressure within the garment above atmosphere over a period of at least about 5 seconds at pressure decay conditions.

21. A disposable containment garment for a wearer, the garment having a body side and an outside, comprising:
a unitary unseamed liquid-impermeable contoured shell comprising an absorbent foam applied over an entire circumference of the body side with a liquid barrier layer, and having an elastic torso and elastic appendage margins which are devoid of gathering and shirring, wherein the liquid barrier layer is selected from the group consisting of polyurethane, styrenic block copolymers, polyether ester, metallocene materials and combinations thereof;

the liquid-impermeable shell having an untensioned humanoid or modified humanoid molding form in substantial conformance with a shape of the wearer;

the elastic margins designed to conformably surround at least a portion of a torso and an appendage of the wearer and form a tensioned and a substantially liquid tight seal against the skin of the wearer;

the liquid tight seal being constructed and arranged to maintain a gas pressure within the garment above atmosphere over a period of at least about 5 seconds at pressure decay conditions.

22. The personal care product of claim 21 wherein the liquid barrier layer is breathable.

23. The personal care product of claim 21 wherein the liquid barrier layer is nonwoven.

* * * * *